(12) United States Patent
Strahilevitz

(10) Patent No.: US 7,166,295 B1
(45) Date of Patent: Jan. 23, 2007

(54) METHODS OF TREATMENT AND DIAGNOSTIC VISUALIZATION, PARTICULARLY IN CANCER

(76) Inventor: Meir Strahilevitz, P.O. Box 190, Hansville, WA (US) 98340

(*) Notice: Subject to any disclaimer, the term of this patent is extended or adjusted under 35 U.S.C. 154(b) by 1756 days.

(21) Appl. No.: 08/451,120

(22) Filed: May 26, 1995

(51) Int. Cl.
| | |
|---|---|
| A61K 9/127 | (2006.01) |
| A61K 9/66  | (2006.01) |
| A61K 9/52  | (2006.01) |
| A61K 9/14  | (2006.01) |
| A61K 9/16  | (2006.01) |

(52) U.S. Cl. .................. 424/450; 424/455; 424/457; 424/489; 424/490; 424/491

(58) Field of Classification Search ............... 424/450, 424/455, 457, 489, 490, 491
See application file for complete search history.

(56) References Cited

U.S. PATENT DOCUMENTS

| | | | |
|---|---|---|---|
| 4,620,977 A | 11/1986 | Strahilevitz | |
| 5,374,548 A * | 12/1994 | Caras | 424/450 |
| 5,431,897 A * | 7/1995 | Welt et al. | 424/1.49 |
| 5,474,772 A | 12/1995 | Maddock | |
| 5,527,528 A | 6/1996 | Allen et al. | |
| 5,620,689 A | 4/1997 | Allen et al. | |

FOREIGN PATENT DOCUMENTS

| | | | |
|---|---|---|---|
| EP | 0302673 | | 2/1989 |
| EP | 0349127 | | 1/1990 |
| WO | 9317715 | * | 9/1993 |
| WO | 9408043 | | 2/1995 |
| WO | 9515770 | | 6/1995 |

OTHER PUBLICATIONS

Gregoriadis & Florence (Drugs, 1993, 45:15-28.*
Gabizon (J. of Liposome Res, 1995, 5:704-710).*
Hird et al (in "Genes & Cancer")Carney et al Ed, John Wiley & Sons, 1990, pp. 83-89.*
Harris et al (Tibtech, 11:42-44, 1993).*
Fahey et al (Clin Exp. Immunol., 1992, 88:1-5).*
Martin et al (Biochemistry, 20:4229-4238), 1981.*
Fanger et al (FASEB, 4;2846-2849), 1990.*
Wong et al (Immunology, 81:280-284), 1994.*
Collins et al (Cancer Res., 47:735-739), 1987.*
C. Lollo et al., Nuclear Medicine Communications, vol. 15, 1994, pp. 483-491.
James L. Lear et al., Radiology, vol. 179, 1991, pp. 509-512.
G. W. Welling et al., Journal of Chromatography, vol. 512, 1990, pp. 337-343.
G. S. David, Biochem. Biophys. Res. Commun., vol. 48, 1972, pp. 464-471.
A. R. Fitzberg et al., Proc. Nat. Acad. Sci. U.S.A., vol. 85, 1988, pp. 4025-4029.
M. belles-Isles and M. Page, British Journal of Cancer, vol. 41, 1980, pp. 841 42.
R. Yang et al., Antibody Immunoconjugates Radiopharmaceuticals, vol. 5(2), 1992, pp. 201-207.
P. Gold and S. O. Freedman, J. Exp. Med., vol. 121, 1965, pp. 439-443.
S. Sell and F. F. Becker, J. Nat. Cancer Inst., vol. 60, 1978, pp. 19-26.
M. Belles-Isles and M.Page, Int. J. Immunopharmacol., vol. 3, 1981, pp. 97-102.
M. Belles-Isles and M. Page, Brit. J. Cancer, vol. 141, 1980, pp. 841-842.
H. Lee et al., Cancer Immunol. Immunotherapy, vol. 5, 1978, pp. 201-206.
David L. Dunn, Arch. Surg., vol. 128, 1993, pp. 1274-1280.
H. Zhao et al., Bioconjug. Chem., vol. 3, 1992, pp. 549-553.
V. S. Reddy and C. H. Ford, Anticancer Research, vol. 13(6A), 1993, pp. 2077-2078.
I. Ahmad and T. M. Allen, Cancer Research, vol. 52, 1992, pp. 4817-4820.
King et al., Antibody Immunoconjugates and Radiopharmaceuticals, vol. 5(2), 1992, pp. 159-170.
M. McClure in: "Encyclopedia of Immunology", Ivan M. Roitt Ed., Academic Press, 1992, pp. 695-700.
K. Y. Hostetler et al., Antimicrob Agents Chemotherapy, vol 38(12), 1994, pp. 2792-2797.
D. D. Lasic and D. Papahadjopoulos, Science, vol. 267, pp. 1275-1276, Mar. 3, 1995.
K. Norrgren et al., Antibody Immunoconjugates and Radiopharmaceuticals, vol. 4 (4), pp. 907-914, 1991.
C. Nicolau and A. Cudd, Critical Reviews in Therapeutic Drug Carrier Systems, vol. 6 (3), 1989.
J. Barbet et al, Journal of Supramolecular Structure and Cellular Biochemistry, vol. 16, pp. 243-258, 1981.
P. Machy and L. D. Leserman, Biochimica Biophysica Acta, vol. 730, pp. 313-320, 1983.

(Continued)

Primary Examiner—Susan Ungar
(74) Attorney, Agent, or Firm—Polster, Lieder, Woodruff & Lucchessi, LC

(57) ABSTRACT

Methods and reagents for improved treatment and diagnostic imaging, particularly of cancer. The methods and reagents utilize specific targeting of treatment and imaging ligands to the targeted tumor, or specific organ or tissue, in association with extracorporeal affinity adsorption of the targeting ligand. The targeted species include antibodies as well as other peptides with specific affinity to the targeted tumor organ or tissue. Included are hybrid targeting molecules, such as hybrid $F(ab')_2$, with one binding site specific for the target and the other binding site specific for the targeted treatment or visualization ligand. The affinity adsorption devices may include adsorbents specific to one or more of the components of the targeting molecule-targeted ligand moiety. The methods provide for improved treatment, particularly in cancer and HIV, by increasing the concentration in the tumor and decreasing the concentration in the rest of the body, thus reducing its toxicity and enabling the use of high doses of drugs and other treatment agents. Improved visualization of cancer is provided by increased concentration of visualization ligand in the cancer and reduced concentration in the blood and normal tissues.

13 Claims, 1 Drawing Sheet

OTHER PUBLICATIONS

G. Adrian and L. Huang, Biochemistry, vol. 18 (25), pp. 5610-5614, 1979.
L. D. Leserman et al., Nature, vol. 293, pp. 226-228, Sep. 17, 1981.
I. Ahmad et al., Cancer Research, vol. 53, pp. 1484-1488, Apr. 1, 1993.
Qian He-nian and Li Wen-jin, Chinese Medical Journal, vol. 106 (5), pp. 343-347, 1993.
P. Machy et al., Proc. Natl. Acad. Sci. USA, vol. 85, pp. 8027-8031, Nov. 1988.
K. Maruyama et al., Proc. Natl. Acad. Sci. USA, vol. 87, pp. 5744-5748, Aug. 1990.
K. K. Matthay et al., Cancer Research, vol. 44, pp. 1880-1886, May 1984.
Y. Hashimoto et al., Cancer Research, vol. 43, 5328-5334, Nov. 1983.
P. Machy et al., The Journal of Immunology, vol. 136 (8), pp. 3110-3115, Apr. 15, 1986.
R. B. Bankert et al., Cancer Research, vol. 49, pp. 301-308, Jan. 15, 1989.
S. S. Williams et al., Cancer Research, vol. 53, pp. 3964-3967, Sep. 1, 1993.
K. Maruyama et al., Proc. Natl. Acad. Sci. USA, vol. 87, pp. 5744-5748, Aug. 1990.
D. D. Lasic et al., Biochimica et Biophysica Acta, vol. 1070, pp. 187-192, 1991.
D. Papahdjopoulus et al., Proc. Natl. Acad. Sci. USA, vol. 88, pp. 11460-11464, Dec. 1991.
"Liposomes as Drug Carriers, Recent Trends and Progress." Gregory Gregoriadis, Editor, John Wiley and Sons Pub., New York, 1988.
P. N. Shek and R. F. Barber in ref. 41, pp. 145-155.
G. Hedlund et al. in ref 41, pp. 167-182.
Irma A. J. M. Bakker-Woudenberg et al., in ref. 41, pp. 325-336.
A. A. Gabizon and Y. Barenholz, in ref. 41, pp. 365-379.
S. E. Seltzer, in Ref. 41, pp. 509,525.
R.J.Y. Ho and L. Huang, in ref. 41, pp. 527-547.
N. Weiner and Chia-ming Chiang, in ref. 41, pp. 599-607.
T. Ghose et al., in ref. 41, pp. 697-707.
T. D. Heath, in ref. 41, pp. 709-717.
L. Leserman, in ref. 41, pp. 719-726.
D. Collins, in ref. 41, pp. 761-770.
C. Hixs and T. R. Witty, Clinical Chemistry, vol. 31 (6), abstract #136 p. 929, 1985.
J. P. O'Connell et al., Clin. Chem. 31/9, pp. 1424-1426, 1985.
Weckenmann, et al.—Arzneim-Forsch/Drug Res. 39 (I), Nr. 3 (1989) pp. 415-420.
B. Geiger, et al.—Eur. J. Immunol. 1981. 11: pp. 710-716.
Ahmad et al, Cancer Research, vol. 53, 1993, pp. 1484-1488.
Allen et al, Journal of Liposome Research, vol. 4(1), 1994, pp. 1-25.
Rational Basis for Chemotherapy, UCLA Symposium Molecular and Cellular Biology, published 1983, Weinstein, J.N., "Target-Direction of Liposomes: Four Strategies for Attacking Tumor Cells", pp. 441-473.
Journal of Liposome Research, Voltage 3. No. 3, issued 1993, Jones et al, "Preparation and Characterization of Ligand-Modified Labelled Liposomes for Solid Phase Immunoassays", pp. 793-804.
Nature, vol. 288, issued Dec. 11, 1980, Leserman et al, "Targetting to cells of fluorescent liposomes covalently coupled with monoclonal antibody or Protein A", pp. 602-604.
Biochemica et Biophysica Acta, vol. 1194, issued 1994, Flasher et al, Liposome Targetting to human immunodeficiency virus type 1-infected cells via recombinant soluble CD4 and CD4 immunoadhesin (CD4-IgG), pp. 185-196, see pp. 193-194.
Henry et al. Improved Monoclonal antibody tumor/background ratios with exchange transfusions. Nuclear Medicine Biology. 1991, Voltage. 18, No. 5, pp. 565-567, see pp. 565.

* cited by examiner

METHODS OF TREATMENT AND DIAGNOSTIC VISUALIZATION, PARTICULARLY IN CANCER

BACKGROUND OF THE INVENTION

One of the major strategies utilized for the improvement of treatment and diagnosis of cancer is to increase the concentration of the anticancer drug in the cancer, by targeting the drug to the cancer, utilizing antibodies and antibody fragments specific to epitopes (antigens) on the cancer cells. This leads to increased therapeutic effect and reduced toxic effects by increasing the ratio of drug concentration in the cancer to the drug concentration in the rest of the body. This strategy is used for enhancing the visualization of the cancer by achieving an increased ratio of isotope concentration in the cancer to the isotope concentration in the rest of the body. Background radioactivity is reduced, cancer radioactivity is increased and cancer visualization is improved.

The methods utilizing direct radioactive labeling by isotopes of targeting antibodies with specific affinity to cancer epitopes are reviewed by C. Lollo et al (Nuclear Medicine Communications, Vol 15, pp 483–491, (1994) Lollo et al also describe an improved targeting method that utilizes hybrid F(ab')$_2$, obtained from two monoclonal antibodies, one with specific affinity to a radiolabeled hapten $^{111}$indium-nitrobenzyl-ethylene diamine tetraacetic acid ($^{111}$In-NBE), and the other with specific affinity to a cancer antigen, carcino embryonic antigen (CEA). An added strategy to the ligand targeting method is utilization of the extracorporeal immunoadsorption methods of U.S. Pat. Nos. 4,834,973 and 4,620,977 to Strahilevitz. These patents disclose methods and devices for the specific removal of ligands from the blood circulatory system and body stores by extracorporeal immunoadsorption of the ligand. James L. Lear et al (Radiology, Vol 179, pp 509–12 (1991)) utilized the methods of the Strahilevitz patents in conjunction with targeting of a visualization ligand. Lear et al utilized a mouse monoclonal antibody with specific affinity to human milk fat globule membrane antigen, which is an epitope (antigen) expressed in many epithelial tumors, including human breast and non-small cell lung carcinomas. The antibody was conjugated with 1-(para-isothiocyanatobenzyl) diethylenetri-amine-pentaacetic acid and the conjugate was radiolabeled with $^{111}$indium. The conjugate was removed from the circulation of the patients by extracorporeal immunoadsorption using as the adsorbent goat antimouse antibody. The addition of the extracorporeal immunoadsorption step was found to increase the ratio of radiolabel concentration in cancer to radiolabel concentration in the rest of the body, and to significantly improve the radiovisualization, when compared to the radiovisualization obtained by use of antibody-targeted radiolabel, without the additional step of extracorporeal immunoadsorption.

SUMMARY OF THE INVENTION

Strahilevitz International patent application PCT/US94/08043, provides for additional improvements in the treatment and visualization, particularly of cancer, by combined ligand-targeting and extracorporeal affinity adsorption (including immunoadsorption) methods, by utilizing in the adsorption step a plurality of adsorbents. In accordance with one aspect of the present invention such methods may include adsorption of antibodies to the cancer, present in the circulation of the patient ("enhancing antibodies"), that may reduce concentration of antibody-targeted ligand in the cancer by competing with the targeting antibody for binding to the cancer epitopes (antigen), or they may include adsorption of circulating tumor antigens which bind the targeting-drug moiety in the blood, thus preventing its targeting to the tumor. These methods include in the affinity adsorption device adsorbents with specific affinity to the enhancing antibody and/or the circulating tumor antigen as well as adsorbents with specific affinity to the targeted ligand. These improvements further increase the efficacy of the combined ligand-targeting extracorporeal affinity adsorption, by further increasing the ratio of ligand concentration in the tumor to that in the rest of the body.

In accordance with one aspect of the present invention, reagents and methods for treating, detecting, and visualizing cancer and other conditions (such as for example, hyperactivity of endocrine glands, for example certain conditions associated with hyperthyroidism) are provided. The novel methods of the invention utilize specific affinity adsorption, both immunoadsorbents as well as non-immune-based specific affinity, biological as well as non-biological chemical affinity adsorbents.

The current invention provides for additional improvement of the combined extracorporeal affinity adsorption-ligand targeting of my International application PCT/US94/08043 by utilizing in the targeting component of the treatment, hybrid antibodies, with specific affinity to cancer epitopes and to the targeted ligand, respectively. The utilization of hybrid antibodies for targeting provides for increased efficacy as compared to other targeting methods used in conjunction with extracorporeal affinity adsorption. Additional augmentation of efficacy is provided by removing with the extracorporeal immunoadsorption, both free ligand and ligand bound to the targeting antibody.

In some situations, such as for example, when the targeting antibody is expensive, particularly when hybrid antibodies are utilized for targeting it is preferable to adsorb in the extracorporeal immunoadsorption step, the free ligand, but not the targeting antibody. Strahilevitz International application PCT/US94/08043 provides for adsorption of the free ligand only. The current application describes utilization of specific adsorption of the free ligand only, when hybrid antibodies are used for targeting.

The current invention also provides for the utilization of liposome or microcapsule entrapment of the targeted ligand in conjunction with extracorporeal immunoadsorption. This will lead to further increased efficacy.

The affinity adsorbents utilized in the present invention can be natural compounds, chemically modified natural compounds, natural compounds modified by biological techniques, such as genetic engineering, as well as specific affinity adsorbents produced by chemical synthesis or genetic engineering methods. The tissue- or tumor-targeting antibodies of the invention can be monoclonal or polyclonal intact antibodies, fragments of antibodies such as Fab', F(ab')$_2$ and Fv fragments of antibodies, produced by enzymatic digestion or by synthesis, including conventional chemical synthesis as well as synthesis by genetic engineering techniques. The targeting ligands may also be single chain and multiple chain epitope-binding peptides produced by chemical synthesis, or by genetic engineering as known in the art. (G. W. Welling et al, Journal of Chromatography, Vol 512, pp 337–343, (1990)). The targeting antibodies and other epitope-binding peptides may be modified to generate "catalytic" antibodies or catalytic epitope-binding peptides as described, for example by Baldwin and Schultz, Science, Volume 245, p 1104–1107 (Sep. 8, 1989). The paper and its references are incorporated herein by reference.

Of particular importance is the utilization of a catalytic function in a tumor-targeting epitope (tumor antigen) binding antibody (or other peptide) when that catalytic function induces an enhanced therapeutic effect such as for example a catalytic function that will increase hydrolysis of constituents of the tumor cell-membrane, thus enhancing delivery of a therapeutic targeted ligand, and otherwise increasing anti-cancer effect, by affecting the integrity of the cancer cell membrane.

The targeting antibody, including fragment is hereafter referred to as "TAB" for abbreviation. Other epitope-binding targeting peptides or proteins are hereafter referred to as "OTP" for abbreviation.

The current invention utilizes a targeted ligand, which may be (a) a treatment ligand (TL) or (b) A visualization ligand (VL).

Treatment ligands include, for example:

a1. Anticancer drug, such as Adriamycin (Doxorubicin)

a2. A radioactive small molecule with molecular weight below 10,000 or radioactive large molecule with molecular weight above 10,000.

a3. A radioactive TAB or OTP, for example a TAB iodinated with $^{131}$I. The TAB or OTP may be directly radiolabeled or it can be conjugated to another molecule which is radiolabeled. (James L. Lear et al, Radiology, Vol 179, pp 509–512 (1991)). References for direct radiolabeling of TAB and OTP are cited in C. Lollo et al, Nuclear Medicine Communications, Vol 15, pp 483–491 (1994). This article and its references are incorporated by reference herein. This references also describe the use of chelating groups that are covalently bound to the TAB. The radiolabel is then attached by its affinity to the chelator.

a4. A biological toxin, such as Ricin A, for example.

a5. A magnetic ligand.

Visualization ligands include, for example:

b1. radiolabeled TAB or OTP, produced by direct radiolabeling such as direct Iodination according to G. S. Davis, Biochem. Biophy Res. Commun., Vol 48, pp 467–471, (1972).

b2. The radiolabel is attached to a bifunctional chelator. (Lollo et al, supra).

b3. Radiolabeling of an intermediary molecule conjugated to the TAB or OTP (A. R. Fritzberg et al, Proc. Nat. Acad. Sci., Vol 85, pp 4025–9 (1988) and J. L. Lear et al supra.

b4. A magnetic ligand.

The TAB or OTB may be associated with the TL or VL by covalent binding. For example, when the TL is Daunomycin, it can be conjugated to the TAB or OTP by utilizing the method of M. Belles-Isles and M. Page, British Journal of Cancer, Vol 41, pp 841–2 (1980). When the TL is Adriamycin, the method of covalent binding via a dextran bridge of R. Yang et al, Antibody Immunoconjugates Radiopharmaceuticals, Vol 5, No 2, pp 201–7 (1992) can be utilized. The TAB or OTP has at least one specific binding site that has high affinity to one of the oncofetal proteins produced by many tumors, such as: carcinoembryonic antigen (CEA), milk-fat globule membrane antigen, alpha fetoprotein (AFT) (P. Gold and S. O. Freedman, J. Exp. Med., Vol 121, pp 439–43 (1965); S. Sell and F. F. Becher, J. Nat. Cancer Inst., Vol 60, pp 9–26 (1978); M. Belles-isles and M. Page, Int. J. Immunopharmac., Vol 3, pp 97–102 (1981); Ibid, Brit. Journal Cancer. Vol 41, pp 841–842 (1980); Lear et al, supra).

The visualization ligand targeted to the tumor or other target, is detected by known methods which are used for such detection, for example scintigraphy external photoscanning, radioimmunoimaging for example use of a gamma camera. (See Lollo et al, supra, and Lear et al, supra) or by known magnetic sensors and scanners. The TAB or OTP can also be specific to fibrin, that coats many tumor cells. H. Lee et al, Cancer Immunotherapy, Vol 5, pp 201–206 (1978).

The TAB or OTP can be specific to a tissue specific antigen, such as thyroid microsomal microvilli antigen, thyroglobulin or thyroid stimulating hormone-receptor. The TL or VL, as described above, can be associated with the TAB or OTP by covalent binding as for example in Rong Yang et al, Antibody, Immunoconjugates and Radiopharmaceuticals, Vol 5, number 2, pp 201–7 (1992).

In many situations it may be preferred to avoid covalent binding of the TL or VL to the TAB or OTP. Instead this binding can be achieved by non-covalent chemical binding. One example for such a method is the utilization of a hybrid antibody with at least one specific binding site directed to the targeted antigen and one binding site directed to the TL or VL. Such a method, utilizing two distinct Fab's and joining them to a hybrid F(ab')$_2$, was produced by the digestion of a monoclonal antibody (MAb) specific to CEA and enzymatic digestion of another MAb specific for the VL $^{111}$Indium-nitrobenzyl-ethylenediaminetetraacetic acid ($^{111}$In-NBE). The two Fab' fragments were covalently bound to form a hybrid F(ab')$_2$ (Lollo et al, supra).

Another component of the treatment and visualization method of the current invention is the use of methods and devices of Strahilevitz U.S. Pat. Nos. 4,834,973 and 4,620,977, and International application PCT/US/94/08043, published as WO 95/03084 on Feb. 2, 1995. All these patents and applications with their references are incorporated by reference herein. These methods and devices include affinity adsorption, affinity dialysis, affinity filtration and affinity diafiltration methods and devices. These methods and devices utilize immunoadsorption and nonimmunologic affinity adsorption. These devices and methods are connected to a biological fluid source of a mammal such as the blood circulatory system. Blood or plasma may be adsorbed; when plasma is adsorbed, a plasma separator is included in the treatment. These methods and devices can also treat peritoneal fluid, if desired, rather then blood or plasma. In the present inventions these methods and devices are used for enhancing the therapeutic effect and the visualization resolution obtained by the other treatment and visualization methods that are also a component of the present invention. It should be realized that other extracorporeal affinity adsorption methods and/or devices, that may or may not be part of the above patents and patent applications, may by utilized in conjunction with the visualization and treatment components of the present invention and when used in conjunction with these methods will be included in the scope of the present invention.

Figure 3:
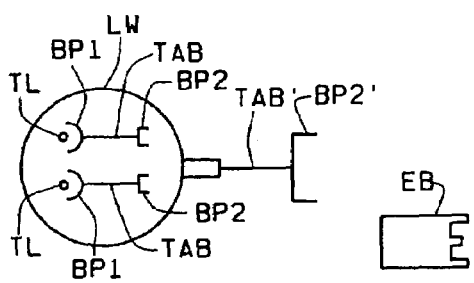
FIG. 3 is a diagrammatic view showing hybrid antibodies bound to a drug and entrapped in a liposome, with a targeting antibody covalently bound to the liposome wall in accordance with another aspect of the invention, together with an antigen for removing hybrid antibody when desired.
Figure 6:
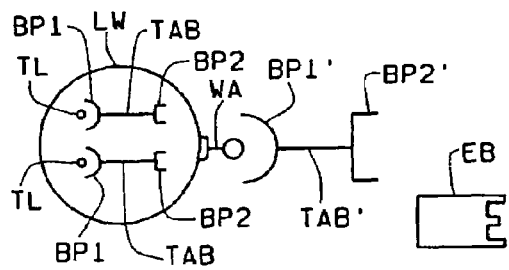
FIG. 6 is a diagrammatic view showing hybrid antibodies bound to a drug and entrapped in a liposome, with a targeting hybrid antibody immunologically bound to an antigen which is covalently bound to the liposome wall in accordance with another aspect of the invention, together with an antigen for removing hybrid antibody.
Figure 7:
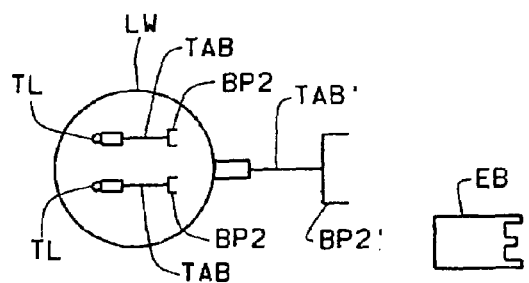
FIG. 7 is a diagrammatic view showing antibodies covalently bound to a drug and entrapped in a liposome, with a targeting antibody covalently bound to the liposome wall, together with an antigen for removing hybrid antibody in accordance with another aspect of the invention.

The Figures illustrate several aspects of the preferred embodiments of the present invention. In the Figures, TL represents a therapeutic ligand (which could equally be a visualizing ligand), TAB represents a targeting antibody, BP1 represents a first binding portion of the TAB, BP2 represents a second binding portion of the TAB, EB represents an extracorporeal binder, LW represents a liposome wall, TAB' represents an antibody bound to the wall of a liposome (it being understood that many such antibodies will usually be bound to the liposome wall), BP1' and BP2' represent binding portions of TAB', and WA represents an antigen or hapten covalently bound to the liposome wall. Illustratively, TL is Adriamycin, BP1 is specific to Adriamycin, BP2 is specific to a tumor antigen such as Le(y) tetrasaccharide or alpha-fetoprotein, and EB is the tumor antigen. Alternatively or additionally, EB may be an antibody specific to Adriamycin, an antibody specific to the TAB, a non-specific immunologic binder such as protein A or protein G, an antibody specific to WA (FIGS. 5 and 6), or an antibody specific to the targeting antibody attached to the liposome wall (FIGS. 3, 6 and 7) when this antibody is different from the antibody entrapped in the liposome.

DESCRIPTION OF THE PREFERRED EMBODIMENT

The following examples illustrate the utilization of the methods and devices of the present invention.

EXAMPLE 1

Use of Hybrid OTP (Hybrid F(ab')2) VL Targeting, in Conjunction with Extracorporeal Affinity clearance of VL Monoclonal antibodies are obtained, using the method of Lollo et al, supra, by immunizing Balb/c mice with the hapten L-SCN-C6H4-CH2-EDTA coupled to the carrier keyhole limpet hemocyanin. After multiple injections, spleen cells are fused with P3-653 myeloma cell line. The clone producing hybridoma CHA-255 is grown in the peritoneal cavity of mice and the MAb isolated from ascites fluid by sodium sulfate fractionation, followed by chromatography purification. Nitrobenzyl-EDTA (NBE) is labeled with $^{111}$Indium according to Lollo et al, supra. The TAB specific to CEA is MAb ZCE-025. Fab' fragments from both MAb ZCE-025 and MAb CHA-255 are prepared and are covalently bound to produce hybrid F(ab')2 with specificity to the hapten $^{111}$In-NBE and the tumor epitope CEA.

Treatment of the patient is as follows. The patient is first injected with the hybrid TAB, in a dose of 0.1 mg/kg to 3 mg/kg, preferably 1 mg/kg, 6–48 hours prior to the injection of the VL (both injections are intravenously). Optionally the VL is injected bound to a MAb or MAb fragment with specific binding affinity for the VL. Alternatively to a two stage injection of the hybrid TAB followed by the free VL, the hybrid TAB and the VL substantially bound to it are injected to the patient in one step. Radiolabeled VL is obtained by the incubation of 10 microgram of NBE-EDTA with 10 mCi of $^{111}$In. Each patient is injected with 4 mCi of VL, injected intravenously over a period of 1 hour. Extracorporeal immunoadsorption is performed 4 to 24 hours after the administration of the VL and continues for 2–8 hours, with a flow rate of 50 ml–200 ml/min, preferably 100 ml/min. The immunoadsorbent is bound to a matrix in an immunoadsorption column, with (optional) online regeneration of the immunoadsorption according to Strahilevitz, U.S. Pat. No. 4,620,997, such as the device utilized by Lear et al, supra, except that the affinity adsorbent is MAb CHA-255, which is covalently bound to the polycarbonate matrix. Approximately 30 mg to 60 mg antibody is bound to the column matrix. Immunoadsorption is continued until 2–3 total plasma volumes (estimated from standard weight-charts) pass through the immunoadsorption column. Total body images are obtained before and following the extracorporeal immunoadsorption step with a gamma camera, Gemini 700 Technicare, GE Medical Systems, as described by Lear et al, supra.

The adsorbent may be the tumor antigen, such as CEA, covalently bound to the matrix in the column. The immunoadsorbent can also be goat antibody to mouse Fab' or mouse F(ab')$_2$; or a combination of two or more of the above adsorbents or other adsorbents that are suitable, depending on the tumor, such as other tumor antigens.

The hybrid antibodies may be "humanized" antibodies produced by the methods described in David L. Dunn, Arch. Surg., Vol 128, pp 1274–1280 (1993) and its references, which are incorporated by reference herein.

When more than one immunoadsorbent is used, rather than incorporating them in a single column, a plurality of columns can be used, with each affinity adsorbent incorporated in each of the columns, utilized in parallel or serially in accordance with Strahilevitz International patent application PCT/US94/08043. In some situations it may be preferable to determine that the patient has a CEA marker bearing tumor, before the utilization of this method. This can be done for example by determining presence of CEA on a small biopsy specimen.

EXAMPLE 2

Use of Hybrid Targeting OTP, with TL

The method is generally similar to the one described in Example 1, except that the treatment ligand is the anticancer drug Adriamycin and the tumor antigen towards which the second F(ab')$_1$ partner of the F(ab')$_2$ hybrid targeting OTP is specific, is the Le(y) tetrasaccharide marker. The OTP is a hybrid F(ab')$_2$ produced by F(ab')$_1$ obtained from MAb BR96, which has specific affinity to Le(y) tetrasaccharide epitope, commonly expressed on human carcinomas. (H. Zhao et al, Bioconjug. Chem. Vol 3, No 6, pp 549–53 (1992)). The MAb specific for Adriamycin (Doxorubicin), is produced according to the method of V. S. Reddy and C. H. Ford, Anticancer Research, Vol 13, No 6A, pp 2077–83 (1993). The hybrid is produced by first obtaining F(ab')$_1$ fragments by enzymatic digestion of the antiadriamycin MAb and the anti Le(y) tetrasaccharide MAb, respectively, as described by Lollo et al, supra, and then the two F(ab')$_1$ fragments are joined by covalent binding, according to Lollo et al to produce the hybrid F(ab')$_2$. Again before the patient is treated, it has to be determined that his tumor bears the Le(y) tetrasaccharide epitope (antigen).

Figure 1:
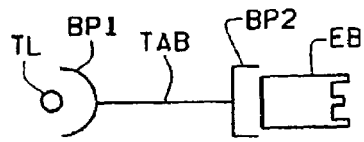
FIG. 1 is a diagrammatic view showing a system of the present invention for delivering an antigen or hapten to a site in an organism and reducing the quantity of the antigen or hapten in the rest of the organism, the system including a hybrid antibody, a drug immunologically attached to the hybrid antibody, and a tumor antigen attached immunologically to another portion of the hybrid antibody.

The dose of Adriamycin is 30 mg to 150 mg/M$^2$ of body surface. The dose of antibody is 0.5–4 gm/M$^2$ body surface. The antibody is administered intravenously 6–36 hours prior to the administration of Adriamycin. Optionally the Adriamycin is injected bound to a MAb or MAb fragment with specific binding affinity for Adriamycin. Alternatively to a two stage injection of the hybrid TAB followed by the free Adriamycin, the hybrid TAB and the Adriamycin substantially bound to it are injected to the patient in one step. The extracorporeal immunoadsorption is started 2–24 hours after completion of administration of Adriamycin, preferably after 4 hours. The affinity adsorbent is an antibody to Adriamycin, or a hapten-binding fragment of the antibody, such as F(ab')$_1$ or F(ab')$_2$. When the antibody is used as adsorbent, the amount of antibody covalently bound to the column of the matrix is 0.5–5 gm. Another affinity adsorbent that can be used is Le(y)-tetrasaccharide (tumor antigen), or an antibody to the hybrid MAb targeting antibody (see FIG. 1).

Figure 2:
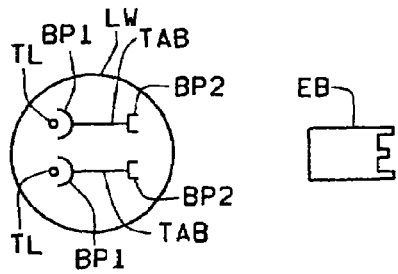
FIG. 2 is a diagrammatic view showing hybrid antibodies bound to a drug and entrapped in a liposome in accordance with another aspect of the invention, together with an antigen for removing hybrid antibody when desired.

A modification of the method includes using a TL TAB, hybrid F(ab')$_2$, with one binding site specific to the Le(y)-tetrasaccharide tumor antigen and the other binding site specific to Adriamycin, with the hybrid F(ab')$_2$, including the Adriamycin, entrapped in liposomes, (see FIG. 2). The immunoadsorbent in the column may include one or more of the following immunoadsorbents: an antibody (or an antigen binding fragment of the antibody) specific to an antigen marker, covalently bound to the liposome's wall, an antibody (or fragment) specific to Adriamycin, an antigen or fragment specific to the targeting antibody (or fragment), tumor antigen (Le(y)tetrasaccharide).

The targeting species, which is covalently bound to Adriamycin, may be an antigen-binding fragment of the targeting MAb, rather than the intact targeting MAb (such as F(ab')$_1$ F(ab')$_2$ or VF fragment). Conjugates of Adriamycin with a targeting MAb, specific to a tumor antigen have been entrapped in liposomes. The liposomes were effective in treating human ovarian carcinoma transplanted in nude mice (W. J. Li et al, Chinese Medical Journal, Vol 74, number 9, pp 539–41 (1994).)

Figure 4:
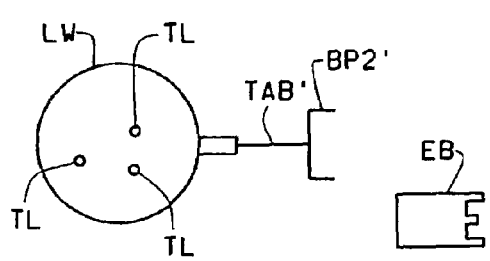
FIG. 4 is a diagrammatic view showing a drug entrapped in a liposome, with a targeting antibody covalently bound to the liposome wall, together with an antigen for removing hybrid antibody in accordance with another aspect of the invention.
Figure 5:
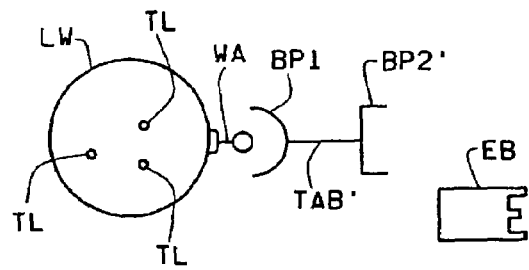
FIG. 5 is a diagrammatic view showing a drug entrapped in a liposome, with a targeting hybrid antibody immunologically bound to an antigen which is covalently bound to the liposome wall in accordance with another aspect of the invention, together with an antigen for removing hybrid antibody.

An additional option is to also target the liposomes to the tumor by covalently binding to the liposome's wall a non-hybrid targeting antibody, with a binding site specific to Le(y)tetrasaccharide tumor antigen. Liposome-entrapped free Adriamycin was targeted to a tumor by Imran Ahmad and Theresa M. Allen (Cancer Research Vol. 52, pp 4817–20 (1992)) by a targeting antibody, covalently bound to the liposome wall. Using this option either free Adriamycin (FIG. 4), or Adriamycin bound to a hybrid targeting antibody can be used (FIG. 5).

Another option is to utilize hybrid antibodies or hybrids of other antigen-binding fragments, such as F(ab')$_2$, with one specificity to the liposome wall and the other binding site with specific affinity to tumor antigen (Le(y)tetrasaccharide) In order to obtain a hybrid antibody with specificity to the liposome wall, it may be necessary to chemically bind an immunoglobulin or immunoglobulin fragment, or any other protein or antigenic peptide, to the liposome wall. When an immunoglobulin or its fragment is used, it is of an isotype different from the isotype of the targeting MAb or other OTP. For example, when the targeting MAb is a mouse MAb, the IgG or IgG fragment that is bound to the liposome wall, will be goat or sheep IgG, or their respective fragment. The binding of the protein or peptide to the wall of the liposome is done in accordance with Ahmad and Allen and its references supra which is incorporated herein by reference. The method of binding used by Ahmad and Allen is a covalent binding, using an avidin-biotin binding method. The hybrid TAB or hybrid OTP has one binding site with affinity for the tumor antigen such as Le(y)Tetrasaccharide epitope, for example. The other binding site has affinity to the protein or peptide bound to the liposome wall (goat IgG, for example).

Either free Adriamycin (FIG. 5) or Adriamycin bound to a hybrid targeting antibody (or fragment) (FIG. 6) may be entrapped in the microcapsule. One binding site of the specific hybrid F(ab')$_2$ used in the example is specific for Adriamycin, the other binding site is specific for Le(y) tetrasaccharide.

The liposomes used may be either conventional liposomes or long-circulating liposomes.

The immunoadsorbent bound to the column matrix may be one or more of the following depending on the particular configuration utilized for the delivery of the Adriamycin to the tumor target (see FIGS. 1–6 for adsorbent suitable for the various delivery options). The immunoadsorbents include tumor antigen (Le(y)tetrasaccharide), antibody to targeting MAb bound to Adriamycin (or its fragment), antibody to targeting MAb bound to liposome wall (or its fragment), antibody to hybrid targeting antibody bound specific to an antigen covalently bound to liposome wall and specific to Le(y)tetrasaccharide, antibody to Adriamycin, antibody specific to antigen that is covalently bound to liposome wall. Whenever the term "antibody" is used, it includes its fragment unless clearly indicated otherwise. Whenever Adriamycin bound non-covalently to its binding site on the hybrid antibody is used, Adriamycin bound covalently to a tumor-targeting antibody (or fragment), can be used instead.

EXAMPLE 3

Use of TL VL Covalently Bound to Targeting OTP, with Extracorporeal Immunoadsorption The method is similar to Example 2 except that the tumor antigen used for targeting is human alpha-fetoprotein (AFP), the targeting species is an intact MAb specific to AFP and the Adriamycin is covalently bound to the targeting MAb as described by Yang et al, supra.

The Adriamycin is covalently linked to a dextran bridge and is then covalently bound to the MAb via the dextran bridge. The treatment protocol is modified in that the targeting MAb that contains about 5–20 moles Adriamycin/mole of MAb is injected in one step. The amount of MAb-Adriamycin conjugate injected, is calculated to administer to the patient 30–150 mg Adriamycin/$M^2$ surface area. The amount of conjugate injected intravenously, will typically be between 350 mg to 1.5 gm.

The extracorporeal immunoadsorption is performed 2–24 hours after the administration of the MAb-Adriamycin conjugate, preferably after 8 hours. The affinity adsorbent consists of one or more of the following: An antibody to Adriamycin, an antibody to the targeting MAb, tumor antigen (AFP). One modification of the method of example 3 is to entrap the Adriamycin that is covalently bound to the tumor targeting MAb (or MAb fragment) in liposomes as described in Example 2. A tumor-targeting MAb or fragment is covalently bound to the liposome's wall, as described in Example 2 (see FIG. 7). As described in Example 2 (FIG. 4), free Adriamycin or targeting antibody-bound Adriamycin can be entrapped in the liposome.

The immunoadsorbent in the extracorporeal device may be one or more of the following: AFP (tumor antigen), antibody to targeting antibody (or targeting fragment), antibody to Adriamycin, antibody to an antigen covalently bound to the liposome wall (as described in Example 2). Clearly all of the methods described in Example 1 can be used with liposome entrapment. (Namely: The liposome entrapment of treatment ligand described in Examples 2 and 3, can be utilized for visualization ligands, both haptenic visualization ligands as well as visualization ligands that are complete antigens.

In all of the examples, the targeting antibody or adsorbing antibody may be modified to induce catalytic property in the antibody (Enoch Baldwin and Peter Schultz, Science, Vol 245, pp 1104–7 (1989)), in order to increase efficiency.

In Examples 1–3 the affinity adsorbent in the extracorporeal immunoadsorption device may include, or may be protein G or staphylococcal protein A, as described in Strahilevitz International patent application PCT/US94/08043, and may include plasma or plasma component replacement. As used herein, staphylococcal protein A and Protein G includes their fragments, including fragments produced by synthesis and genetic engineering.

In all of the examples the TAB-TL or OTP-TL (or TAB-VL or OTP-VL) can be injected intraarterially, when localized administration is preferred, such as in the treatment of liver cancer, with hepatic arterial infusion (J. Matsumoto et al, Japanese Journal of Cancer and Chemotherapy, Vol 20 No 11, pp 1538–41 (1993)).

As previously described, whenever targeting antibodies (TAB) are used, other targeting proteins or peptides (OTP) can be used instead. Included in OTP are antigen binding fragments such as: $F(ab')_2$, $F(ab')_1$, Fv as well as smaller synthetic antigen binding proteins. TABs and OTPs (including Fv fragment) can be produced by genetic engineering methods, in accordance with King et al, Antibody Immunoconjugates and Radiopharmaceuticals, Vol. 5, number 2, pp 159–170 (1992). King et al also describe the production of "humanized" MAbs and OTPs by genetic engineering methods. Such fragments produced according to King et al, or by other known methods, can also be utilized as the immunoadsorbents in the extracorporeal affinity device.

When liposome encapsulation of TL or VL is used for targeting, with covalent binding of antigen to the liposome's wall and the use of hybrid antibody or hybrid OTP, for targeting, with one binding site specific for the tumor antigen and the other binding site specific for the antigen that is covalently bound to the liposome's wall, the same antigen can be used for targeting the liposome to the tumor and for immunoadsorption of the nontargeted liposomes (which dissociated from the targeting hybrid antibody). However, another alternative is to covalently bind two distinct antigens to the liposome's wall, one for hybrid antibody mediated targeting and another as the immunoadsorption "marker" for the antibody (or fragment) immunoadsorbent in the extracorporeal device. In that case the immunoadsorbent will be specific for the second antigen bound to the liposome's wall. In this option, both liposomes that are bound to hybrid targeting antibody and liposomes that are dissociated from the hybrid targeting antibody will be adsorbed to the affinity adsorbent.

Liposomes with antigen or hapten (covalently bound to protein or peptide carriers) which are covalently (or noncovalently) bound to the liposome wall, may have numerous utilizations.

For example, it can be used to increase the sensitivity of immunoassays, such as for example radioimmunoassay. Known antigen or hapten protein or hapten peptide conjugate, is covalently bound to the liposome wall. A radioactive tracer of choice (such as 131-iodinated protein) is entrapped in the liposome. The unknown antibody is coated on the wall of a suitable, (preferably plastic) tube. A known amount of the above prepared liposome is added to the test tube. After incubation the tube is emptied and washed. If the antibody is specific for the antigen, the radioactive liposomes will remain bound to the antibody which is adsorbed to the test tube, as a result of the affinity of the antibodies to the antigen (or hapten) covalently bound to the radioactive liposome's wall. This has increased sensitivity, due to the ability to target a substantially larger amount to radioactivity to the adsorbed antibody, by using the entrapped radioactive tracer in the liposome.

A modified system can be used for detecting or quantifying antigen or hapten. The antibody adsorbed to the tube's wall is specific to the antigen (or hapten) bound covalently to the liposome's wall. Again a radioactive tracer is entrapped in the liposome. Adding a sample that contains the antigen or hapten will inhibit the binding of the radioactive liposomes to the antibody, proportionally to the amount of antigen or hapten in the sample.

Such an "inhibition assay" can be used for the assaying of samples for presence and amount of a specific antibody in a sample. Again, a known amount of the antibody is coated on the wall of the test tube. Antigen or hapten is covalently bound to the radioactive liposome's wall. Presence of the specific antibody in the sample will lead to proportional inhibition of the binding of radioactive liposomes to the antibody that is bound to the test tube wall.

In another modification, the known antibody is covalently bound to the liposome wall and the respective antigen is covalently bound to the test tube wall for determining antigens and antibody presence in a tested sample in an "inhibition" assay.

Antibody bound radioactive liposomes can similarly be used in a "direct assay" by evaluating presence of protein or peptide antigens in a sample that are adsorbed to the test tube wall.

Clearly, other tracers than radioactive tracers, such as a color tracer, for example fluoresceinated protein or peptide, can be entrapped in the liposome and determined by known methods.

Clearly it should be realized that, with respect to the utilization of the devices and methods of the current invention for the treatment of cancer, when targeting of antineoplastic drugs is part of the treatment, any of the antineoplastic drugs can be utilized as long as a specific antibody is available, or can be made available, that has specific affinity for the drug, or alternatively, whenever the antineoplastic drug can be covalently bound to a targeting antibody or other targeting protein or peptide. Antibodies are available for many of the antineoplastic drugs. Methods to covalently bind many of the drugs to proteins and peptides are known or can be easily determined. The antineoplastic drugs include: antibiotics, such as Adriamycin+; (Doxorubicin) and Daunorubicin+; steroids, such as progestines; plant alkaloids, such as vinblastin+; pyrimidine antagonists such as fluorouracil; Purine antagonists, such as 6 mercaptopurine; Antimetabolites (structural analogs), such as methotrexate+; Alkylating agents, such as Chlorambucil+; Antiestrogen, such as Tamoxifen+. At least one benzene ring is present in these molecules marked with +.

While immunological affinity binding species may be, in many utilizations, the binding species of choice for affinity binding to specific targets in the organism, as well as the specific affinity adsorbents, in many utilizations of the present invention, nonimmunologic affinity binding species may be the binding species of the utilizations of the methods of the invention.

Nonimmunologic affinity binding species include for example:

1. Enzymes with selective affinity to a site in an organism.
2. Synthetic drugs with selective affinity to receptors in the organism, such as haloperidol that has selective affinity to the D2 receptor and the drug Atenolol that has specific affinity to the beta-1-adrenergic receptor. It is well known that many of the drugs have specific affinity to specific receptors in the organism.
3. Hormones which have selective affinity to receptors, such as Thyroid Stimulating Hormone (TSH), which has selective affinity to it's receptors in the Thyroid gland.

Clearly the above species can also be used as the specific affinity adsorbents, when removal of targeted ligands, is included in the treatment method. Thus, Thyroid TSH-receptor can be used for affinity adsorption of TSH. D2 receptors can be used for the affinity adsorption of neuroleptics such as haloperidol.

Of particular interest is the utilization of the methods of the invention in the treatment of individuals with HIV infection (AIDS). A critical element in the pathogenesis of HIV infection, is the attachment of the virus via its glycoprotein gP 120 envelope, to the CD 4 molecule, which is present in T4 Helper lymphocytes and some other cells. The binding of the HIV virus to the CD4 molecule is of very high affinity and specificity. Small fragments of the extracellular domain of the CD4 molecule have been shown to block viral infectivity and the N-terminal V1 domain alone can block HIV infection in vitro. This blocking of infection is mediated by attachment of the CD4 derived fragment to the HIV's gP 120 glycoprotein blocking the virus from infecting CD4 bearing cells. Myra McClure in *Encyclopedia of Immunology*, Ivan M. Roitt Editor, pp 695–700, Academic Press, 1992.

Anti-HIV drugs such as Dioleoyl-phospathidyl-ddc (DOP-ddc) and Dipalmitoyl-phosphatidyl-3'-Azido-3'-deoxythymidine (DPP-AZT) were incorporated in liposomes that were injected intraperitoneally into mice were associated with increased concentration of drug in the plasma, spleen and lymphoid tissue relative to the concentration obtained by the injection of the respective free drugs. (K. Y. Hostetler et al., Antimicrob Agents Chemother, Vol. 38 number 12, pp 2792–7 (1992).

In accordance with the present invention an anti-HIV treatment agent is entrapped in liposomes in free form or bound to a hybrid targeting moiety, with one binding site specific to the drug and the other binding site specific to a target on the virus. The hybrid targeting moiety may be a hybrid of two antibodies or two antibody fragments, or it may be a hybrid of one antibody or antibody fragment specific to the drug with the other component of the hybrid targeting moiety being a CD4 fragment, specific to the virus target.

An HIV-infection inhibiting, preferably synthetic, CD4 derived peptide is directly, preferably covalently, bound to the liposome wall, or is bound to the liposome wall indirectly, via binding to another protein that is covalently bound to the liposome wall. The liposome is administered to the HIV infected individual, preferably intravenously, leading to the targeting of the liposomes containing large amounts of drugs to the HIV virus. Clearly, such an approach can be used in the treatment of other viral diseases and other infectious diseases such as bacterial and protozoal diseases. Clearly, in accordance with the present invention, hybrid antibodies or OTP, with one binding site specific to the antigen covalently bound to the liposome's wall and the other binding site specific to a target epitope on the HIV virus can be used for targeting instead of the CD4-derived targeting moiety. Alternatively, the targeting antibody or OTP with affinity to the HIV virus can be covalently bound to the liposome's wall in accordance with Ahmad and Allen, supra. Alternatively, the anti-HIV drug in the liposome is covalently bound to a ligand targeting the HIV virus.

A step of affinity adsorption may optionally be added to the treatment in order to enable treatment of the patient with relatively high doses of drug, for a predetermined period of time, thus reducing drug toxicity to the patient.

When liposomes are used for treatment or visualization in accordance with the invention, they are either injected or in some applications, particularly when no TAP or OTP is bound to the wall of the liposome, they may be administered orally.

Numerous other variations, within the scope of the appended claims will be apparent to those skilled in the art.

I claim:

1. A method of delivering a ligand to a site in an organism, the method comprising a step of binding to the surface of a moiety selected from the group consisting of a liposome and a microcapsule a first molecule targeting the site, a step of entrapping a ligand in the moiety, the ligand being bound to a second molecule targeting the site, and thereafter a step of introducing the moiety into the organism.

2. The method of claim 1 wherein at least one of the first molecule and the second molecule comprises a drug having affinity for the site.

3. The method of claim 1 wherein at least one of the first molecule and the second molecule comprises a hormone having affinity for the site.

4. The method of claim 1 wherein the moiety is a liposome.

5. The method of claim 1 wherein the moiety is a microcapsule.

6. The method of claim 1 including a further step of removing from the organism at least one of the moiety and the ligand by affinity adsorption.

7. The method of claim 6 wherein the affinity adsorption is immunoadsorption with an antibody to the ligand.

8. The method of claim 1 wherein said first molecule targeting the site is a protein or peptide.

9. The method o claim 8 wherein said first molecule targeting the site comprises an antibody.

10. The method of claim 9 wherein said antibody is an antibody fragment.

11. The method of claim 10 wherein said second molecule targeting the site comprises an antibody.

12. The method of claim 1 wherein said second molecule targeting the site comprises an antibody.

13. The method of claim 1 wherein the first molecule targeting the site has affinity for the same site as the second molecule targeting the site.

* * * * *